United States Patent [19]

Rozich

[11] Patent Number: 5,141,646
[45] Date of Patent: Aug. 25, 1992

[54] PROCESS FOR SLUDGE AND/OR ORGANIC WASTE REDUCTION

[75] Inventor: Alan F. Rozich, Wilmington, Del.

[73] Assignee: Environmental Resources Management, Inc., Exton, Pa.

[21] Appl. No.: 668,070

[22] Filed: Mar. 12, 1991

[51] Int. Cl.⁵ ............................................. C02F 11/02
[52] U.S. Cl. ................................... 210/613; 210/623; 210/631; 210/903; 210/906
[58] Field of Search ............... 210/605, 607, 609, 612, 210/613, 620–622, 631, 903, 906

[56] References Cited

U.S. PATENT DOCUMENTS

| | | | |
|---|---|---|---|
| 3,356,609 | 12/1967 | Bruemmer | 210/7 |
| 3,547,814 | 12/1970 | McWhirter | 210/7 |
| 3,622,507 | 11/1971 | Pasveer | 210/631 |
| 3,670,887 | 6/1972 | McWhirter | 210/5 |
| 4,026,793 | 5/1977 | Rein | 210/12 |
| 4,159,944 | 7/1979 | Erickson et al. | 210/631 |
| 4,246,099 | 1/1981 | Gould et al. | 210/613 |
| 4,267,049 | 5/1981 | Erickson et al. | 210/609 |
| 4,277,342 | 7/1981 | Hayes et al. | 210/613 |
| 4,652,374 | 3/1987 | Cohen | 210/603 |
| 4,721,570 | 1/1988 | Ankaitis | 210/619 |
| 4,849,108 | 7/1989 | de Wilde et al. | 210/605 |
| 4,882,068 | 11/1989 | Blom | 210/703 |
| 4,915,840 | 4/1990 | Rozich | 210/605 |

Primary Examiner—Thomas Wyse
Attorney, Agent, or Firm—Nixon & Vanderhye

[57] ABSTRACT

A process for the treatment of organic waste is described which comprises the steps of:
a) feeding input waste in an input line to an ATAD reactor where the waste is subjected to biological digestion;
b) settling out a portion of a biomass formed in the digestion unit;
c) hydrolyzing the separated portion in a hydrolysis vessel;
d) returning hydrolyzed effluent to the input line upstream of the ATAD reactor; and
e) periodically removing clear decant from the reactor. Variations of this process include removal of nutrients from the clear decant; feeding solid organic waste by a grinder upstream of the mixer; feeding the mixed material initially to an AAD vessel from which methane gas is removed, and then to the ATAD reactor, with or without nutrient removal.

19 Claims, 2 Drawing Sheets

1

PROCESS FOR SLUDGE AND/OR ORGANIC WASTE REDUCTION

TECHNICAL FIELD

This invention relates to treatment of organic waste in general, and to an improved process for the treatment of sludge and/or solid organic waste.

BACKGROUND OF THE INVENTION

Numerous aerobic processes have been developed over the years for the biological treatment of municipal waste which includes both domestic and industrial sewage for yielding an environmentally acceptable effluent. One of the widely-used aerobic processes for such treatment is referred to as the activated sludge process wherein organic matter contained in the municipal waste is contacted with an oxygen-containing gas in the presence of suspended biologically active organisms under conditions such that the organic material is converted into a form which can be separated from purified water. A portion of the insoluble sludge that is formed is recycled to the aerobic zone. Another is the trickling filtration method wherein the microorganisms are fixed to a support.

As is known in activated sludge systems and other aerobic processes, e.g., the trickling filtration process, there is usually a significant net positive production of sludge containing suspended solids in the process and there is an increasing inventory of sludge. Excess sludge must be discarded on a periodic basis from the process. Biological sludges produced by the activated sludge process and other aerobic processes are difficult and expensive to treat because these sludges have poor dewatering properties and are highly putrescible. Because of these characteristics, sludge disposition has become an important problem in the environmental conservation area. Ocean dumping of sludge or use as landfill are objectionable in the environment conservation arena because such sludges present health hazards to the environment. Prior to disposal, these sludges require pasteurization so that the concentration of pathogenic organisms is sufficiently low to avoid potential health hazards.

Numerous processes have been developed for sludge stabilization and one process traditionally used has been anaerobic digestion. In anaerobic processes, the organic material present in the sludge is oxidized to by-products such as organic acids, ammonia, and principally methane. One of the problems associated with anaerobic digestion is that it is high cost in operation and substantial time is required for the digestion process. Thus equipment tends to be of a large scale.

Another process for stabilizing activated sludge is referred to as extended aeration wherein the sludge is contacted in an aerobic digestion zone and the organic material oxidized over time. Although extended aeration may offer significant advantages over anaerobic digestion, there are problems associated with such processes because of high operating expenses and capital costs associated with the extended residence time required to effect biological oxidation.

There are many variations in processes associated with the aerobic treatment of municipal waste which includes an activated sludge concept or alternate aerobic processes for handling the net for excess production of sludge. Such process are described in the following references and these include:

U.S. Pat. No(s). 3,547,814 and 3,670,887 disclose the treatment of sewage wherein gross solids are first removed from the sewage by screening and the remaining waste contacted with an oxygen-containing gas and activated sludge. The '814 patent discloses that anaerobic processes have been used to render the sludge nonputrescible and as noted require long-term storage, e.g., 30 days, etc. Even after such treatment, the residual solids from the process comprise from 40-50% of the original volume of excess sludge. Another suggested technique for treating such sludge involved extended aeration which increased the degree of auto-oxidation, i.e., the sludge became self-consuming to some degree, and there was a net reduction of such sludge. Unfortunately, the rate of oxidation was generally too low to have a significant effect on net sludge production. Even with extended aeration and increased degree of auto-oxidation, particularly at the zero net production of sludge level, problems were presented because of large plant size and high operating costs. For example, capacities were three to six times larger than a conventional activated sludge plant. To reduce size, the patentees suggested using an oxygen-rich gas and a high volatile organic material in the sludge. This resulted in a low sludge yield in the overall process.

U.S. Pat. No. 3,356,609 discloses a process for treating municipal waste wherein the initial sewage is clarified generating a bottoms fraction or raw sludge and effluent containing suspended or soluble organic matter. The effluent is then enriched with a carbon source and contacted with an oxygen-containing gas and activated sludge in a dispersed culture aerobic reactor. The product from the dispersed culture aerobic reactor is contacted with a flocculent and separated. The sludge formed then is separated in a secondary clarifier and a portion recycled to the aerobic reactor and the excess, along with the raw sludge from the primary clarifier, oxidized in a sludge aerobic reactor.

U.S. Pat. No. 4,246,099 discloses a combination of aerobic/anaerobic concepts to reduce and stabilize sludge solids in an activated sludge process. In this process, municipal sludge was initially contacted with an oxygen-containing gas under aerobic conditions to partially reduce the biodegradable volatile suspended solids and then anaerobically digested to partially-stabilize the sludge. Sludge reduction to less than 40% of the biodegradable volatile suspended solids introduced to the digestion zone was achieved. The concept thermal aerobic digestion was referred to as auto-thermal aerobic digestion wherein the digester was operated at elevated temperatures, e.g., from about 45°–75° C. or the thermophilic range. As the patentees indicated, the mesophilic microorganism population declined while the thermophilic forms increased and the rate of biological digestion increased at these higher temperatures.

U.S. Pat. No. 4,026,793 discloses an aerobic digestion process for reducing the solids content in a biodegradable organic sludge by carrying out the digestion in a vessel maintained at a temperature within the range of 38°–46° C. This temperature was alleged to enhance the development of protozoa Monodidae and thus enhance the reduction of solids in the sludge.

U.S. Pat. No. 4,652,374 discloses a modified anaerobic fermentation of municipal waste by effecting hydrolysis and acidification of the sewage and then anaerobically digesting the hydrolyzed sewage under conditions for methane generation.

It is also known in a modified extended aeration, activated sludge process in combination with autothermal aerobic digestion (ATAD) to use a hydrolytic assist which comprised the treatment of the effluent from the ATAD with acid and subjecting the resulting hydrolyzed effluent to biological digestion in the initial aeration zone wherein the sewage was contacted with an oxygen-containing gas and activated sludge. *Proceedings*, 17th Conference on Municipal Sludge Management, HMCRI, Boston, Mass., 1907, pp. 71-77.

As can be seen from the review of substantial prior art pertaining to aerobic processes, including activated sludge processes, many variations have been proposed in an effort to reduce or minimize sludge production and to stabilized excess sludge produced by aerobic processes. All of these processes in one way or another become quite complex and may exhibit high operating costs or capital costs in order to achieve that objective. In most cases, it is extremely difficult to modify these processes in such a way that there is substantial sludge reduction, based on original organic input, let alone achieving sludge elimination. The latter goal is one often sought but seldom achieved and typically requires intervening physical separation processes such as dewatering and subsequent incineration. Removal of organics from waste streams via respiration and conversion into microbial mass and its subsequent conversion to water and carbon dioxide is seldom achieved.

In my prior U.S. Pat. No. 4,915,840, which is expressly incorporated herein by reference, there is disclosed an improvement for sludge reduction in an aerobic process wherein municipal waste containing organic matter is biologically digested by contact with an oxygen-containing gas in the presence of biologically active organisms. In the basic process, and with reference to FIG. 1, municipal sewage is charged through input line 2 to a primary clarifier (PC) 3 wherein separable solids primarily comprising sand and grit, as well as insoluble organics, settle via gravity generating an effluent containing suspended organic material and a solid fraction. The effluent containing suspended solids, e.g., from 50 to 500 mg/l is removed through line 4 and enters aerobic or aeration zone 6. In this aeration zone, an oxygen-containing gas, e.g. air, or oxygen-rich stream, is introduced through line 8 and dispersed within the aqueous medium contained in aeration zone 6. Aeration zone 6 contains biologically active organisms in the form of activated sludge and the conditions are controlled within aeration zone 6 such that from about 50 to about 80 of the organic matter in the form of volatile suspended solids and nitrogen and some phosphorus supplied with the effluent from line 4 is biologically digested. Typically, the concentration of volatile suspended solids within the aeration zone will range from about 1,000 to 5,000 mg per liter.

Aerating devices within aerobic zone 6 are designed to enhance oxygen transfer into the aqueous medium and such transfer usually is measured by determining the dissolved oxygen in the aqueous medium. To insure that sufficient oxygen is present in aeration zone 6, oxygen must be introduced at a rate at least equal to that rate at which it is consumed, and preferably in excess of such rate, which is usually evidenced by a measured dissolved oxygen content in the aeration zone. Usually the dissolved oxygen content is at least 0.1 part per million parts (ppm), and preferably above 1 ppm.

A mixed liquor containing suspended solids generated in aerobic zone 6 is carried by line 10 to secondary or final clarifier 12 (CLAR) wherein the separable solids in the mixed liquor are settled to form a heavy sludge and a purified effluent. The purified effluent overflows in secondary clarifier 12 and is removed from the process through line 14 and may be subjected to further treatment prior to disposal. Optional treatments of the purified effluent include chlorination, as noted in zone 16, and then it is discharged from the process through line 18.

A heavy sludge is withdrawn from secondary clarifier 12 through line 20 and a portion constitutes recycle activated sludge for aerobic zone 6. The recycle activated sludge is charged to aerobic zone 6 via line 22 along with effluent from line 4 and recycled (to be discussed) at a rate sufficient to provide a volatile suspended solids content of at least 50%, and preferably within a range of from 1,000 to 5,000 mg/l in aerobic sludge zone 6. To maintain activity, the recycle of activated sludge is preferably done quickly and under conditions such that the biologically active organisms are not deprived of oxygen during this transfer.

The balance of heavy sludge from secondary clarifier 12 is withdrawn and removed via line 24 and charged to vessel 26 for accommodating adjustment of the solids content of the activated sludge. Typically, the solids content of the activated or heavy sludge withdrawn from secondary clarifier 12 ranges from about 0.5 to 1.5% solids. This sludge is combined with the clarified sediment containing from 2-5% solids from primary clarifier 3 via line 27. Depending upon the level of sludge generation in the overall process, the concentration of solids in secondary thickening vessel 26 is increased and adjusted to a level of from about 3 to 10% by weight. Vessel 26 (TH) generally utilizes conventional mechanical apparatus for secondary thickening of concentrating the activated sludge. However, chemical flocculating agents can be added to achieve desired solids concentration. The activated sludge of preselected suspended solids content of 3 to 10% by weight is withdrawn from vessel 26 through line 28. A portion is withdrawn from line 28 through line 30 for further treatment in hydrolysis vessel 31 (to be described). A portion of hydrolyzed sludge removed through line 32 for combination with thickened sludge from line 28 and then charged via line 33 to autothermal aerobic digester zone (ATAD) 34.

The biological digestion of sludges in an autothermal aerobic digestion unit (ATAD) is a known process and discussions of autothermal thermophilic aerobic digestion techniques are set forth in a paper presented at the 40th annual Purdue Industrial Waste Conference, West Lafayette, Ind. May 14-16, 1985 entitled "Autothermal Thermophilic Aerobic Digestion in the Federal Republic of Germany" and in U.S. Pat. No. 4,246,099, the subject matter of which is also incorporated by reference. In autothermal aerobic digester zone 34, air, or other oxygen-containing gas, e.g., high purity oxygen, is introduced through line 36 at a rate sufficient for the autothermal thermophilic aerobic digestion of the suspended solids. In this process, a temperature of from about 35°-75° C. is maintained, and the heat generated in the process should be sufficient to maintain temperature without external heating. These autothermal self-heating units contain the metabolic heat generated and require no external heat addition to maintain the autothermal digest at appropriate conditions. The nonconverted product containing organic material of preselected concentration usually from 0.5 to 2% solids, is removed as effluent from autothermal aerobic digester zone 34 via line 35 and all or a portion charged to initial aeration digester zone 6. The recycle plus recycle from secondary clarifier 12 is adjusted to give the desired preselected sludge value. With appropriate decay in autothermal digester zone 34, no net sludge generation is possible. That portion not charged to aerobic zone 6 is removed through line 39 for disposal.

To control sludge reduction to a preselected value, and for total sludge elimination, a portion of the thickened biologically activated sludge is withdrawn from line 28 through line 30 wherein it is contacted in hydrolysis vessel 31 (HYD) with acid e.g., sulfuric acid or base, e.g., alkali metal hydroxide under conditions sufficient to effect hydrolysis of macromolecular components of the organic cells and effect dissolution of inorganic components. Mild acid hydrolysis is achieved in vessel 31 by adding acid and maintaining a pH in the range of from about 0.5 to 2 at a pressure ranging from atmospheric to about 30 psig at temperatures ranging from about 80° to 130° C. for about 2 to 10 hours typically about 4-6 hours. Alkaline hydrolysis can also be effected and this is achieved by contacting with alkaline materials, e.g., sodium hydroxide and maintaining a pH of from about 7 to 12 and a temperature of 20° to 50° C. for about 5 to 12 hours. This hydrolytic assist modifies the cell structure of the macromolecular components and renders them essentially soluble and thereby enhances the ability of the biologically active organisms to effect thermophilic decay within the autothermal aeration digester zone 34. By increasing or decreasing the amount of the thickened sludge subjected to hydrolysis one increases or decreases the rate of decay for the system and sludge reduction levels can be controlled by controlling the rate of such decay and thus, the extent of decay.

Hydrolyzed sludge not charged to autothermal aerobic digestion zone 34 may be treated for removal of phosphorous or nitrogen or may be adjusted in pH for optimizing decay in the autothermal aerobic digestion zone. Hydrolyzed sludge is withdrawn from vessel 31 through line 38 and charged to tank 40 wherein pH, for example, is adjusted upwardly to an alkaline level for precipitation of phosphorus compounds which are then removed through line 42. The balance of material in vessel 40 is removed through line 44 and charged to autothermal aerobic digester zone 34.

Further details relating to my prior process and variations thereof can be obtained with reference to U.S. Pat. No. 4,915,840.

In accordance with the present invention, an improved yet simplified process for treating sludge is provided. In a first exemplary embodiment, sludge is charged directly to an ATAD reactor from a mixing vessel to provide immediate digestion. During periodic quiescent periods, a portion of settled biomass is removed from the ATAD reactor and charged to a hydrolysis unit for treatment with a strong acid or base solution. The settled biomass is permitted to hydrolyze for a period of time, preferably at least about six hours, and is then returned to the mixing chamber upstream of the ATAD reactor. The hydrolysate is mixed with the incoming sludge which is then fed directly to the ATAD reactor. The incoming sludge neutralizes the hydrolyzed stream to bring it to a desired pH 7. The hydrolyzed sludge, which is above room temperature, also helps to heat up the incoming feed sludge. Periodically, purified decant is removed from the ATAD reactor and returned to the plant.

In another exemplary embodiment of the invention, a process similar to that described above is employed but additional process steps are applied to the purified decant. Specifically, phosphate and nitrogen are removed from the decant line and the treated decant is then returned to the plant. The nitrogen is removed, preferably biologically or by air stripping of ammonia, and the phosphorous is removed preferably by precipitation. This additional nutrient removal step will also remove other dissolved solids which may pose a problem in downstream treatment processes.

In a third exemplary embodiment of the invention, a system for the treatment of solid organic waste is provided which is similar to the embodiments described above but wherein a grinder is included upstream of the mixing chamber and is used to reduce particle size and to make the incoming solids more amenable to biodegradation via liquid composting. The nutrient removal system described above in the second exemplary embodiment may or not be utilized as desired in this third embodiment.

In a fourth exemplary embodiment of the invention, an energy generation system is provided wherein feed sludge or solid waste is introduced to a grinder and is then fed to a mixer. The sludge or solid waste is then introduced to an autothermal anaerobic digestion unit (AAD) which is similar to an ATAD reactor except that it requires a higher input solids concentration and no oxygen is utilized. From the AAD unit, a settled biomass may optionally be removed and charged to a hydrolysis unit and the hydrolyzed biomass returned to the mixing chamber. Decant from the AAD unit is fed to an ATAD reactor from which a settled biomass is also charged to the hydrolysis unit. ATAD decant is then removed from the ATAD unit and, optionally, processed through the nutrient removal system as described above.

Thus, in its broader aspects, the present invention provides a process for the treatment of organic waste comprising the steps of:
a) feeding input waste in an input line to an ATAD reactor where the waste is subjected to biological digestion;
b) settling out a portion of a biomass formed in the digestion unit;
c) hydrolyzing the separated portion in a hydrolysis vessel;
d) returning hydrolyzed effluent to the input line upstream of the ATAD reactor; and
e) periodically removing clear decant from the reactor.

In a related aspect, the present invention provides a process for the treatment of solid organic waste comprising the steps of:
a) grinding the solid organic waste;
b) feeding ground solid organic waste to a mixer;
c) feeding the ground and mixed solid organic waste to an ATAD reactor;
d) settling out a portion of a biomass formed in the ATAD reactor;
e) hydrolyzing the separated portion in a hydrolyzed vessel;
f) returning hydrolyzed effluent to the mixer; and g) periodically removing clear decant from the ATAD reactor.

In still another aspect, the present invention provides a process for treatment of waste comprising the steps of:
a) feeding input waste to an AAD vessel;
b) feeding AAD decant from the AAD vessel to an ATAD reactor;
c) settling out a portion of biomass formed in the ATAD reactor;
d) hydrolyzing the settled ATAD biomasses in a hydrolysis vessel;
e) returning hydrolyzed effluent to a mixer upstream of the AAD vessel for mixing with the input waste;
f) extracting methane gas from the AAD vessel; and
g) periodically removing clear decant from the ATAD reactor.

Each of the processes set forth above may be modified to the extent of removing nutrients, i.e., nitrogen and phosphorous from the clear decant. Other variations will be described further herein.

The above described process and variations thereof, provides increased sludge reduction in a more efficient manner which requires fewer chemicals and therefore less cost, as compared to the prior art processes.

Other objects and advantages will become apparent from the detailed description which follows.

DETAILED DESCRIPTION OF THE DRAWINGS

Figure 1:
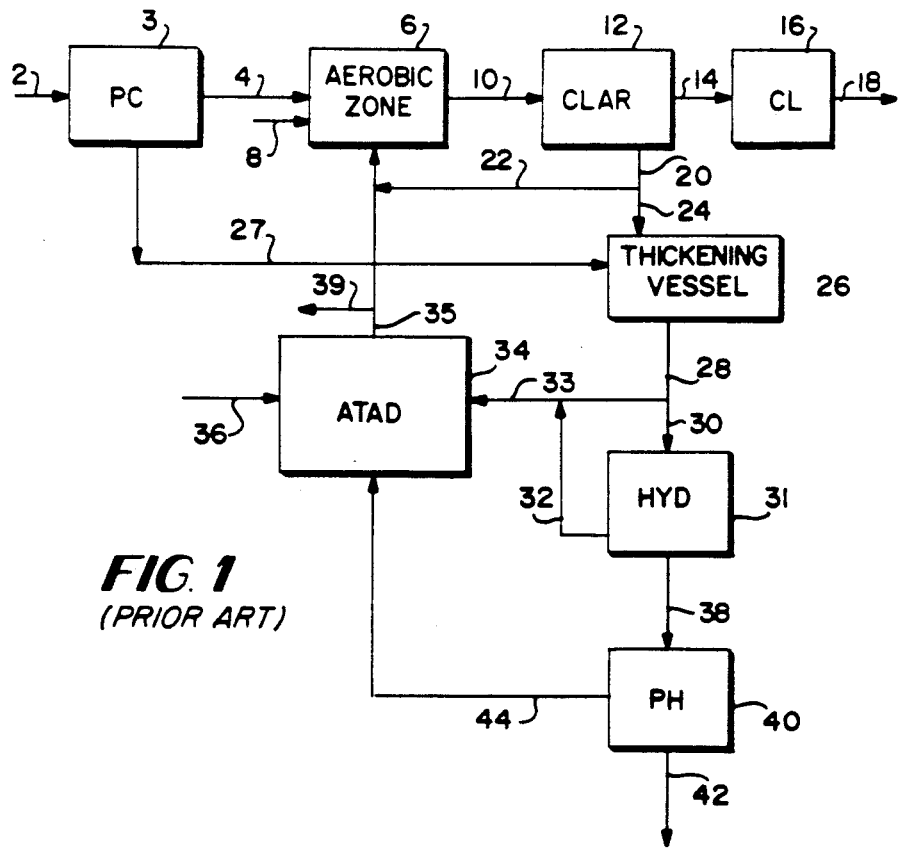
FIG. 1 is a block flow diagram of an activated sludge process incorporating a hydrolytic assist for an autothermal aerobic digestion zone (ATAD) for enhanced sludge reduction as described in my prior patent.
Figure 2:
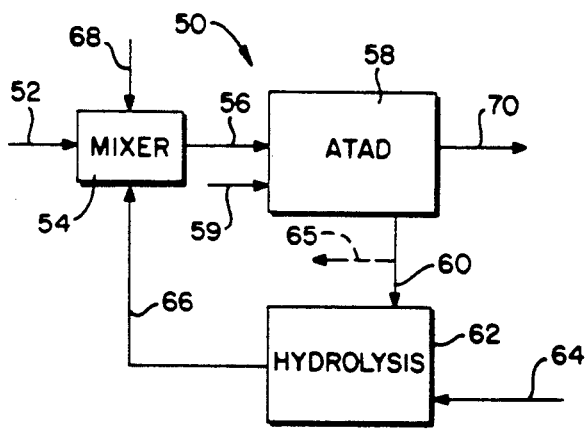
FIG. 2 is a flow flow diagram of an activated sludge process in accordance with one exemplary embodiment of this invention.

With reference now to FIG. 2, a system 50 for treatment of sludge is illustrated where sludge, comprising at least 4% solids, is charged through an input line 52 to a mixing vessel 54 and thereafter via line 56 to an ATAD reactor unit 58. The function of the mixer 54 will be described further herein.

In the ATAD reactor unit 58, an autothermal thermophilic aerobic digestion process as described above is effected at about 50°-70° C. Air or other oxygen containing gas is introduced via line 59 into the ATAD reactor 58 at the appropriate rate for the aerobic digestion of the suspended solids in the reactor. Periodically, for example, once daily, the ATAD reactor unit 58 is shut down and the biomass within the reactor is allowed to settle during a quiescent period (preferably about ½ to 1 hour). Thereafter, a portion of the settled biomass, and preferably between 1 and about 10 of the ATAD reactor biomass, is withdrawn from the ATAD unit 58 and is charged via line 60 to the hydrolysis vessel 62 for treatment with a strong acid or base. The dosage is preferably about 1 part acid or base (added to vessel 62 via line 64) to about 10 parts solids on a mass basis. If needed, excess sludge may be removed upstream of the hydrolysis vessel via line 65. The biomass is allowed to hydrolyze for at least six about hours.

The hydrolyzed biomass is then introduced via line 66 to the mixing vessel 54 where it mixes with the incoming feed sludge from line 52. In this way, the incoming feed sludge neutralizes the hydrolyzed stream, bringing it closer to a desired pH 7. If needed, further pH adjustment can be effected by addition of an acid or base via line 68.

It will be further appreciated that the hydrolyzed sludge added to the mixer 54 is warm, thereby helping to raise the temperature of the incoming sludge from feed line 52, and thereby further reducing cost by eliminating the need for separate heating equipment.

Periodically, a purified clear decant is removed from the ATAD unit 58 and returned to the plant via line 70.

There are a number of advantages to feeding the sludge first to the ATAD reactor 58 and then hydrolyzing the ATAD biomass as described above in the unit 62. Specifically, it has been determined to be beneficial to expose the sludge to the biologically active organisms in the ATAD reactor as a first step in the process, as opposed to introducing the sludge to an aeration zone, a secondary clarifier, and to hydrolysis prior to introduction into the ATAD reactor as in my prior '840 patent. In accordance with this invention, recalcitrant materials from the ATAD reactor are hydrolyzed at about 50°-70° C. which allows a more efficient hydrolysis with less acid or base required. In addition, the influent sludge in the present exemplary embodiment of the invention can be utilized to neutralize the hydrolyzed stream which effects a savings in chemicals required for the process. Further, the above described arrangement permits the utilization of heat from the hydrolyzed stream to raise the temperature of the sludge which results in a more efficient hydrolyzing treatment. Finally, the treated sludge, i.e., the ATAD biomass, is in a condition such that it can be disposed at off-site locations without further treatment.

Figure 3:
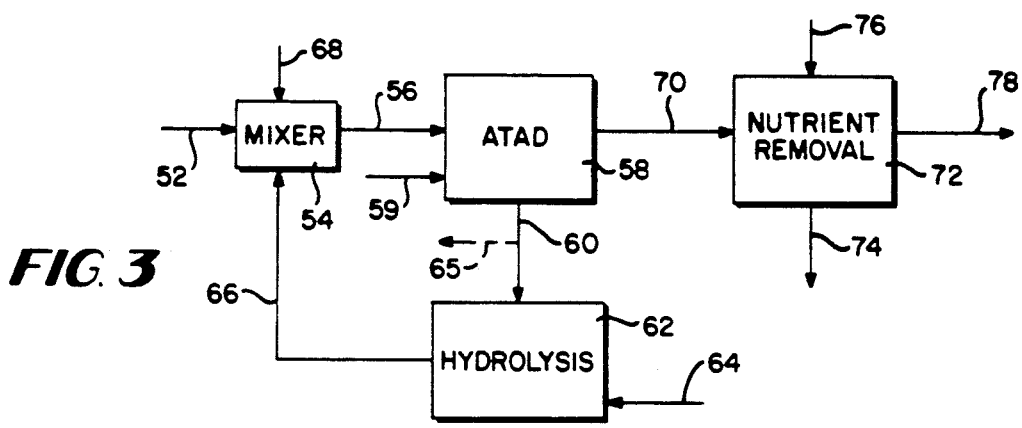
FIG. 3 is a flow flow diagram of an activated sludge process in accordance with another exemplary embodiment of this invention.

FIG. 3 illustrates another exemplary embodiment of the invention which is similar to the embodiment described hereinabove relative to FIG. 2, but which enables the removal of nutrients from the decant line 70. Specifically, FIG. 3 illustrates a nutrient removal station 72 which receives purified decant from the line 70 (reference numerals in FIG. 3 correspond to those used in FIG. 2 for common elements), and is treated to remove nitrogen and phosphorous. In this embodiment, chemicals are added via line 76 to the nutrient removal station 72 while phosphate/chemical sludge is removed via line 74. The treated decant is then returned to the plant via line 78.

In this second exemplary embodiment, the phosphorous is removed from the decant preferably by precipitation, while nitrogen is removed preferably biologically or by other suitable means, such as air stripping of ammonia. Heretofore, it had not been recognized that nitrogen and additional phosphorous would be produced in an ATAD reactor during digestion. Thus, the suggested mode of nutrient removal in my earlier '840 patent is inefficient by comparison. It will be appreciated that nutrient removal will also remove other dissolved solids which may pose a problem in other downstream treatment processes.

Figure 4:
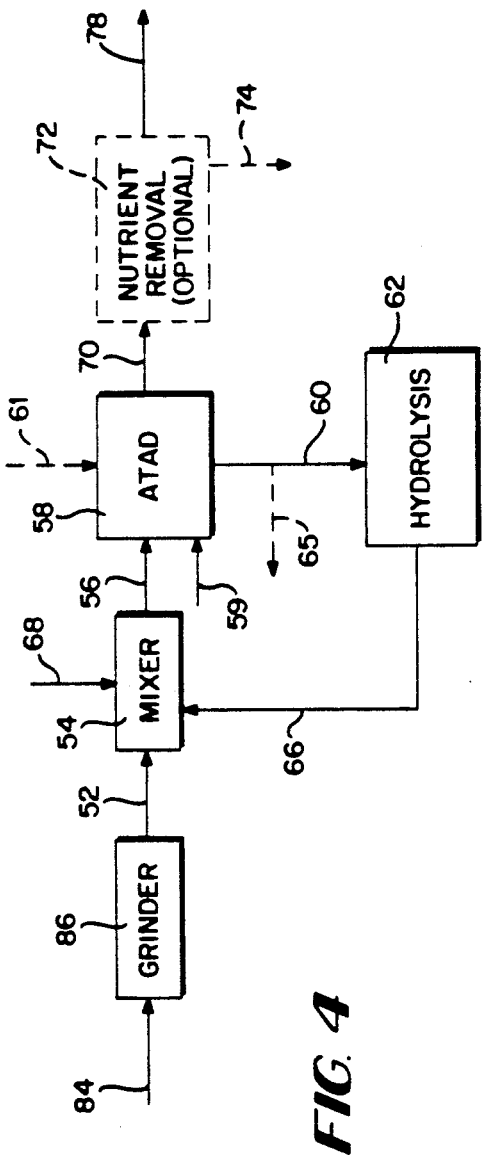
FIG. 4 is a flow flow diagram of an activated sludge process in accordance with another exemplary embodiment of this invention.

With reference now to FIG. 4, a third exemplary embodiment of the invention is disclosed for treatment for solid organic wastes. Here again, elements in common with the previously described embodiments utilize identical reference numbers. In this third exemplary embodiment, an arrangement similar to that shown in FIG. 3 is utilized with the addition of a grinder upstream of the mixer 54. Specifically, a trash stream comprising at least 4% solids is introduced via a line 84 into a grinder 86 which is operatively connected via line 52 to the mixer 54. The grinder is utilized in this embodiment to reduce particle size and to convert the solids to a more amenable state for biodegradation via liquid composting. Thus, this system is appropriate for treatment of trash, garbage, leaves, grass clippings and so on. As a further feature of this embodiment, water and/or nutrients may be added to the ATAD reactor 58 via line 61 if desired.

A significant advantage of the above described arrangement is that since nutrients may need to be added for some types of solid organic wastes, using the above described method where the ATAD biomass is hydrolyzed, allows nutrients to be recycled to the process via mixer 54, thereby conserving chemical usage.

The nutrient removal step described above with respect to FIG. 4 may be employed if desired, with the final preferred product returned to the plant via line 78.

Figure 5:
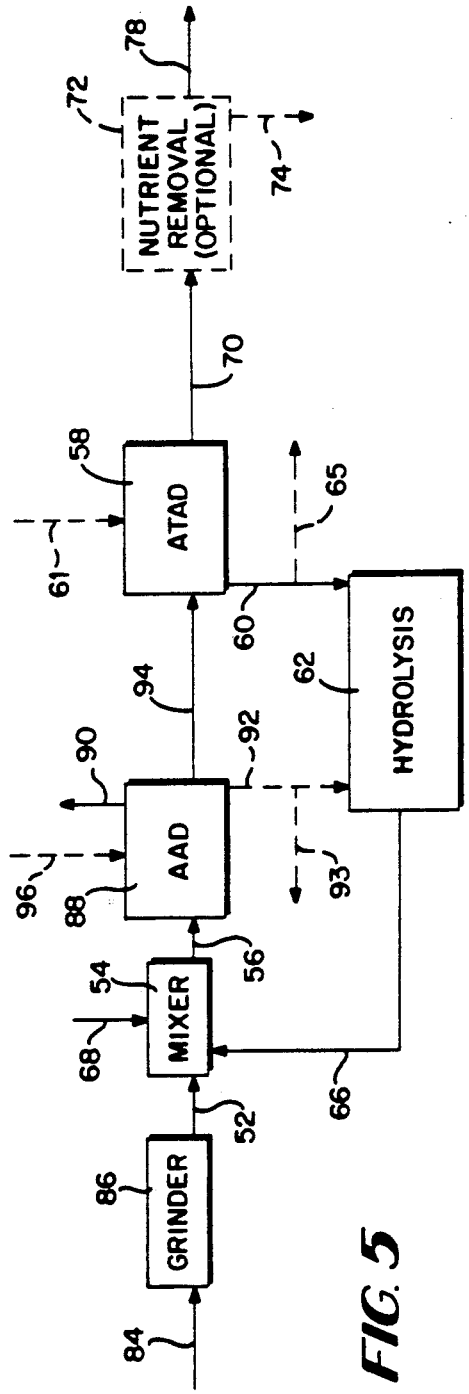
FIG. 5 is a flow flow diagram of an activated sludge process in accordance with another exemplary embodiment of this invention.

In FIG. 5, a fourth embodiment of the invention is disclosed in the context of an energy generation system which extracts methane gas from sludge/trash prior to composting.

In this fourth embodiment, the sludge or solid waste comprising approximately 8% solids may be fed to the grinder 86 via line 84 and thereafter to the mixer 54 via line 52. The sludge is thereafter passed via line 56 to an autothermal anaerobic digestion (AAD) unit 88 where methane gas is drawn off via line 90. Optionally (via line 92), settled biomass from the AAD unit may be hydrolyzed in the unit 62 and recirculated to the mixing chamber 54. If necessary, excess sludge may be removed via line 93 upstream of the hydrolysis vessel 62.

The AAD unit 88 is an autothermal anaerobic digestion device. It is similar to the ATAD reactor 58 except that it requires higher input solids concentration and it is anaerobic, so that no oxygen (aeration) is supplied. The AAD unit is designed to extract energy from the sludge or trash prior to ultimate stabilization via composting. Water and/or nutrients may be added to The AAD unit, if desired, via line 96. AAD decant from unit 88 is fed to the ATAD reactor 58 via line 94.

A portion of the ATAD biomass is settled and removed as before, and returned to the hydrolysis unit 62 via line 60, the hydrolyzed stream feeding into mixer 54 via line 66. Purified decant from the ATAD reactor may be returned to the plant via line 70, or introduced into a nutrient removal device 72, as described above. Treated decant is returned to the plant via line 78.

Thus, in accordance with the above described invention, a simpler, more economical and more effective process is provided by which virtually all of the organic sludge is eliminated, leaving only a clear decant liquid which may be returned to the plant for further processing.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A process for treating of organic waste comprising the steps of:
    a) feeding input waste in an input line to an ATAD reactor where the waste is subjected to biological digestion;
    b) settling out a portion of a biomass formed in the digestion unit;
    c) hydrolyzing the separated portion in a hydrolysis vessel;
    d) returning hydrolyzed effluent to the input line upstream of the ATAD reactor; and
    e) periodically removing clear decant from the reactor.

2. The process of claim 1 and including the step of mixing input waste and hydrolyzed effluent upstream of said ATAD reactor unit.

3. The process of claim 2 wherein an acid or base is added in the mixing step.

4. The process of claim 2 wherein a pH of about 7 is achieved in the mixing step.

5. The process of claim 2 wherein the input waste comprises solid organic waste.

6. The process of claim 5 and including the step of grinding the solid organic waste upstream of the mixing step.

7. The process of claim 6 and including the further step of removing nitrogen and phosphorous from the clear decant.

8. The process of claim 1 wherein the input waste comprises at least 4% solids.

9. The process of claim 1 wherein a temperature of about 50°-70° C. is maintained in said ATAD reactor.

10. The process of claim 9 wherein a temperature of about 50°-70° C. is also maintained in the hydrolysis vessel.

11. The process of claim 1 wherein excess sludge is removed between the ATAD reactor and the hydrolysis vessel.

12. The process of claim 1 and including the further step of removing nitrogen and phosphorous from the clear decant.

13. The process according to claim 12 wherein the nitrogen is removed biologically.

14. The process according to claim 12 wherein phosphorous is removed by precipitation.

15. The process of claim 1 wherein the input waste comprises sludge.

16. A process for the treatment of solid organic waste comprising the steps of:
    a) grinding the solid organic waste;
    b) feeding ground solid organic waste to a mixer;
    c) feeding the ground and mixed solid organic waste to an ATAD reactor;
    d) settling out a portion of a biomass formed in the ATAD reactor;
    e) hydrolyzing said separated portion in a hydrolyzed vessel;
    f) returning hydrolyzed effluent to said mixer; and
    g) periodically removing clear decant from said ATAD reactor.

17. The process of claim 16 wherein said solid organic waste comprises at least 4% solids.

18. The process of claim 17 and including the further step of removing nutrients from the decant.

19. The process of claim 18 wherein said nutrients include nitrogen and phosphorous.

* * * * *